(12) United States Patent
Makarychev et al.

(10) Patent No.: US 10,750,724 B1
(45) Date of Patent: Aug. 25, 2020

(54) SYSTEM, APPARATUS, AND METHOD FOR MONITORING AN ANIMAL STATUS

(71) Applicant: Averia Electronics, Inc., New York, NY (US)

(72) Inventors: Yury Makarychev, Volgograd (RU); Stanislav Terekhov, Krasnoselec (RU)

(*) Notice: Subject to any disclaimer, the term of this patent is extended or adjusted under 35 U.S.C. 154(b) by 0 days.

(21) Appl. No.: 16/818,451

(22) Filed: Mar. 13, 2020

Related U.S. Application Data

(63) Continuation-in-part of application No. 16/564,408, filed on Sep. 9, 2019.

(30) Foreign Application Priority Data

Mar. 11, 2019 (RU) .................. 2019106674
Mar. 13, 2019 (EA) ..................... 20190499

(51) Int. Cl.
*H04W 64/00* (2009.01)
*A01K 29/00* (2006.01)
*H04W 4/021* (2018.01)

(52) U.S. Cl.
CPC ........... *A01K 29/005* (2013.01); *H04W 4/021* (2013.01)

(58) Field of Classification Search
None
See application file for complete search history.

(56) References Cited

U.S. PATENT DOCUMENTS

| | | |
|---|---|---|
| 2017/0202180 A1 | 7/2017 | Yang |
| 2017/0332330 A1 | 11/2017 | Dhandu |
| 2018/0064068 A1 | 3/2018 | McKee |
| 2019/0213860 A1* | 7/2019 | Shaprio ............... H05K 5/0086 |

* cited by examiner

*Primary Examiner* — Suhail Khan
(74) *Attorney, Agent, or Firm* — Ellenoff Grossman & Schole LLP; James M. Smedley; Alex Korona

(57) ABSTRACT

A method is disclosed. The method includes providing a monitoring device to an animal, the animal being monitored by a user having a user device, determining location data defining a spatial zone, determining location data of the monitoring device, sensing a movement of the animal using the monitoring device, and determining whether or not the monitoring device is connected to the user device via a first communication system when the movement of the animal exceeds a movement threshold. The method also includes determining whether or not the monitoring device is connected to a second communication system when the monitoring device is not connected to the user device via the first communication system, and determining whether or not the monitoring device is located in the spatial zone by comparing the location data defining the spatial zone with the location data of the monitoring device.

20 Claims, 5 Drawing Sheets

SYSTEM, APPARATUS, AND METHOD FOR MONITORING AN ANIMAL STATUS

RELATED APPLICATIONS

This application is a continuation-in-part application of and claims the benefit of U.S. patent application Ser. No. 16/564,408 filed Sep. 9, 2019, which claims the benefit of Russian patent application number RU2019106674 filed Mar. 11, 2019, and Eurasian patent application number EA201990499 filed Mar. 13, 2019, each of which is hereby incorporated by reference in its entirety.

TECHNICAL FIELD

The present disclosure generally relates to a system, apparatus, and method for monitoring a status, and more particularly to a system, apparatus, and method for monitoring an animal status.

BACKGROUND

Conventional techniques exist for notifying a user of a location of an animal location using a tracker installed the animal's collar. Such systems typically involve transmitting location data of an animal from the collar to a user.

For example, U.S. patent application number US2017/332330 published Nov. 16, 2017, discloses sending animal location data to a user's electronic device. U.S. patent application number US2018/064068 published Mar. 8, 2018, discloses using an electronic animal collar to receive data from various modules and from a user's electronic device to determine an animal location. US2017202180 published Jul. 20, 2017, discloses receiving data from, e.g., sensors and an animal owner's smartphone to determine a coefficient for animal safety.

Disadvantages of the above conventional methods include the high risk of errors involved in analyzing large data volumes and/or determining safe coefficients. Such high risk of error often leads to an incorrect determination of safe zones for animal location and/or erroneous animal safety statuses. These deficiencies often lead to repeated false alarms and cause anxiety to an animal owner, which incorrectly reflect animal safety statuses and degrade the quality of safe status determinations of animals in conventional systems.

The exemplary disclosed system, apparatus, and method are directed to overcoming one or more of the shortcomings set forth above and/or other deficiencies in existing technology.

SUMMARY OF THE DISCLOSURE

In one exemplary aspect, the present disclosure is directed to a method. The method includes providing a monitoring device to an animal, the animal being monitored by a user having a user device, determining location data defining a spatial zone, determining location data of the monitoring device, sensing a movement of the animal using the monitoring device, and determining whether or not the monitoring device is connected to the user device via a first communication system when the movement of the animal exceeds a movement threshold. The method also includes determining whether or not the monitoring device is connected to a second communication system when the monitoring device is not connected to the user device via the first communication system, determining whether or not the monitoring device is located in the spatial zone by comparing the location data defining the spatial zone with the location data of the monitoring device, and transferring alert data to the user device when the monitoring device is not located in the spatial zone.

In another aspect, the present disclosure is directed to a system. The system includes an animal status module, comprising computer-executable code stored in non-volatile memory, a processor, a monitoring device, and a user device. The animal status module, the processor, the monitoring device, and the user device are configured to determine location data defining a safe geographic zone, determine location data of the monitoring device, sense a movement of an animal using the monitoring device, and determine whether or not the monitoring device is connected to the user device via a first communication system when the movement of the animal exceeds a movement threshold. The animal status module, the processor, the monitoring device, and the user device are also configured to determine whether or not the monitoring device is connected to a second communication system when the monitoring device is not connected to the user device via the first communication system, determine whether or not the monitoring device is located in the safe geographic zone by comparing the location data defining the safe geographic zone with the location data of the monitoring device, and transfer alert data to the user device when the monitoring device is not located in the safe geographic zone. Each of the first communication system and the second communication system is either a Bluetooth system or a Wi-Fi network

DETAILED DESCRIPTION AND INDUSTRIAL APPLICABILITY

The exemplary disclosed system, apparatus, and method may include determining the safe status of an animal using an electronic monitoring device. In at least some exemplary embodiments, the exemplary disclosed system, apparatus, and method may include monitoring a status of an animal using an electronic collar or a microchip, which can be applied to an animal by owners of pets or farm animals.

The exemplary disclosed system, apparatus, and method may include monitoring and/or determining whether a status of an animal is safe or unsafe for example depending on geographic location, surrounding conditions, and/or any other suitable factors. The exemplary disclosed system, apparatus, and method may include any suitable animal status monitoring application such as, for example, maintaining a pet in a yard or other predetermined area, maintaining livestock, managing tracked animals (e.g., such as endangered species), and/or any other desired application for monitoring animal statuses.

Figure 1:
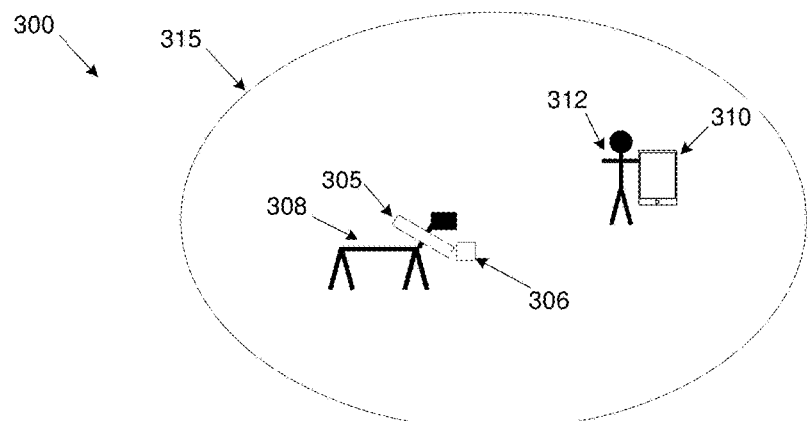
FIG. 1 illustrates an exemplary disclosed system of at least some exemplary embodiments of the present disclosure.
Figure 2:
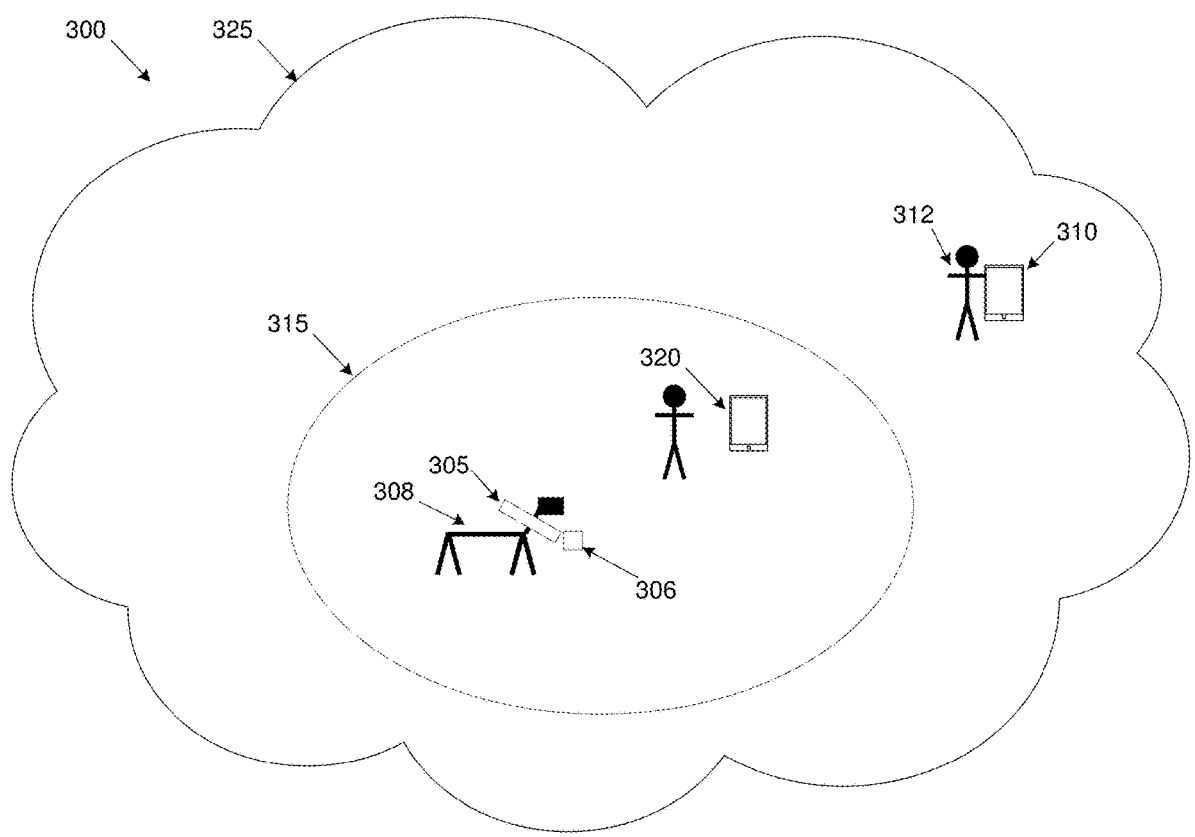
FIG. 2 illustrates an exemplary disclosed system of at least some exemplary embodiments of the present disclosure.

In at least some exemplary embodiments and as illustrated in FIGS. 1 and 2, the exemplary disclosed system, apparatus, and method may include a system 300. System 300 may include one or more monitoring devices 305, one or more user devices 310, one or more communication systems 315, one or more user devices 320, and/or one or more communication systems 325. Monitoring device 305, user device 310, and/or user device 320 may transmit and receive data via communication systems 315 and 325. User device 320 may or may not be co-located with a user.

Monitoring device 305 may be any suitable device that may be attached to, embedded in, and/or worn by an animal 308 (e.g., such as a dog, cat, hamster, mouse, rat, horse, mule, donkey, cow, sheep, pig, whale, dolphin, seal, shark, bird, or any other desired pet, livestock, marine animal, or other animal that may move over land, sea, and/or in the air). Monitoring device 305 may be a collar (e.g., an electronic collar), a smart ring or a smart bracelet, or any other suitable device that may be worn by animal 308. Monitoring device 305 may also be a microchip that may be attached to the skin or embedded in the body of animal 308. Monitoring device 305 may communicate with other devices of system 300 (e.g., user device 310 and/or user device 320) via communication systems 315 and/or communication system 325 (e.g., via Bluetooth, Wi-Fi network, and/or any other suitable communication technique). Monitoring device 305 may include position-finding components such as Global Positioning System (GPS) components, Global Navigation Satellite System (GNSS) components, and/or similar components that may determine a geographic location of animal 308. For example, monitoring device 305 may include a GNSS module and/or components, a communication module and/or other suitable components. In at least some exemplary embodiments, monitoring device 305 may communicate using any suitable communication technique such as Global System for mobiles (GSM), narrow band (e.g., narrow band IoT such as LTE Cat1, LTE-M, NB-IoT), Wi-Fi, and/or Bluetooth (e.g., including the Bluetooth Low Energy or BLE standard). Monitoring device 305 may include any suitable communication components such as a 2G/3G modem and/or components for operation with 4G and/or 5G networks.

Monitoring device 305 may include any suitable sensors for sensing data associated with animal 308. For example, monitoring device 305 may include location sensors (e.g., GPS and/or GNSS components as disclosed above) and/or sensors for sensing a rate of change of a position of animal 308 such as an accelerometer. For example, monitoring device 305 may include a displacement sensor, a velocity sensor, inclinometer, and/or an accelerometer. Monitoring device 305 may include sensors for sensing a body temperature of animal 308, a change in ambient temperature (e.g., a thermometer), a level or intensity of lighting, an ambient humidity, and or any other suitable parameters. Monitoring device 305 may also include a heartbeat sensor for sensing a heartbeat of animal 308. For example, monitoring device 305 may include a temperature sensor, a humidity sensor, and/or a light sensor (e.g., light intensity, illumination, and/or any other similar suitable sensor), communication modules or components (e.g., BLE, Wi-Fi, narrow band, and/or GNSS components or modules), a SIM chip (e.g., a SIM chip or an eSIM chip), an accelerometer, a water sensor (e.g., a humidity sensor), and/or a thermometer. For example, monitoring device 305 may include an eSIM chip that may be updated remotely (e.g., may run software that allows it to be updated remotely or over the air). The eSIM chip may allow for its profile to be changed (e.g., updated remotely) if system 300 is transitioned between providers or carriers (e.g., between cellular, Wi-Fi, network, or other providers or carriers). For example, if providers or carriers of system 300 are changed, a carrier profile of the exemplary disclosed eSIM of monitoring device 305 may be updated remotely (e.g., which may avoid a manual replacement of chips based on a carrier or provider being changed).

In at least some exemplary embodiments, monitoring device 305 may include a location sensor that measures a geographic location such as, for example, a geo-positioning sensor. For example, the location sensor may be a global positioning system sensor or any other suitable type of sensor for sensing location with suitable accuracy. For example, the location sensor may provide a precise location of animal 308 co-located with monitoring device 305 of within about 10 feet, within about 5 feet, within about 3 feet (e.g., within about 3½ feet, for example, within 3.6 feet), and/or within about 1 foot.

In at least some exemplary embodiments, monitoring device 305 may include an ambient pressure, altitude, and/or temperature sensor that may determine an altitude or other geographic position information based on a sensed atmospheric pressure and/or a sensed temperature. The sensors may determine a location and/or altitude directly based on, for example, communicating with a global positioning system or other position location system. Also for example, monitoring device 305 may include a ranging device and/or a sounding device. In at least some exemplary embodiments, monitoring device 305 may communicate with an exemplary disclosed user device (e.g., a smartphone operating with iOS or Android) below 433 mHz radio frequencies via a radio antenna that may be connected to the exemplary disclosed user device (e.g., via a system radio antenna that may be plugged into the exemplary disclosed user device using any suitable port such as USB type-C or Lightning) for any suitable application such as for providing security (e.g., rangers or police) or for hunting. Monitoring device 305 may sense an altitude above sea level (e.g., or any other desired reference point for measuring altitude or elevation). Monitoring device 305 may include for example a barometer or any other suitable device for sensing a barometric pressure (e.g., ambient pressure). Monitoring device 305 may include any suitable sensing components such as, for example, a thermocouple, a resistance temperature detector (RTD), a thermistor, and/or a semiconductor-based temperature sensing component. Monitoring device 305 may include any suitable integrated sensor or sub-array of sensors for determining an ambient pressure, position data (e.g., geographic location and/or altitude or elevation), and/or a body temperature of animal 308 and/or an ambient temperature at a location of monitoring device 305.

Monitoring device 305 may include a controller that may control an operation of monitoring device 305. The controller may include for example a processor (e.g., microprocessing logic control device) or board components. Also for example, the controller may include input/output arrangements that allow it to be connected (e.g., via wireless, Wi-Fi, Bluetooth, or any other suitable communication technique) to other components of system 300. For example, the controller may control an operation of monitoring device 305 based on input received from an exemplary disclosed module of system 300 (e.g., as described below), user devices 310 and 320, and/or input provided directly to monitoring device 305 by a user (e.g., via any suitable user interface provided on monitoring device 305 such as a keypad, button, and/or a touchscreen). The controller may communicate with components of system 300 via wireless communication, Wi-Fi, Bluetooth, network communication, internet, and/or any other suitable technique (e.g., as disclosed herein).

Monitoring device 305 may include any suitable communication components. For example, monitoring device 305 may include any suitable type of receiver device (e.g., a Wi-Fi/Bluetooth receiver). Monitoring device 305 may include any suitable transceiver device (e.g., transmitter device and/or receiver device) for transmitting data to other components of system 300 and also for receiving data from other components of system 300. Monitoring device 305 may wirelessly transmit and/or receive data by any suitable technique such as, e.g., wirelessly transmitting data via any suitable network, Bluetooth, Wi-Fi, wireless Internet, and/or any other desired technique. Monitoring device 305 may transmit and/or receive data at any desired constant or variable interval and/or substantially continuously.

Monitoring device 305 may be formed from any suitable materials for a wearable device for animal 308 such as, for example, Polycarbonate (PC), Barium (e.g., BaSO$_4$), silicone material, polymer material, structural metal (e.g., structural steel), co-polymer material, textile material, thermoplastic and thermosetting polymers, resin-containing material, polyethylene, polystyrene, polypropylene, epoxy resins, phenolic resins, Acrylanitrile Butadiene Styrene (ABS), Mix of ABS and PC, Acetal (POM), Acetate, Acrylic (PMMA), Liquid Crystal Polymer (LCP), Mylar, Polyamid-Nylon, Polyamid-Nylon 6, Polyamid-Nylon 11, Polybutylene Terephthalate (PBT), Polycarbonate (PC), Polyetherimide (PEI), Polyethylene (PE), Low Density PE (LDPE), High Density PE (HDPE), Ultra High Molecular Weight PE (UHMW PE), Polyethylene Terephthalate (PET), PolPolypropylene (PP), Polyphthalamide (PPA), Polyphenylenesulfide (PPS), Polystyrene (PS), High Impact Polystyrene (HIPS), Polysulfone (PSU), Polyurethane (PU), Polyvinyl Chloride (PVC), Chlorinated Polyvinyl chloride (CPVC), Polyvinylidenefluoride (PVDF), Styrene Acrylonitrile (SAN), Teflon TFE, Thermoplastic Elastomer (TPE), Thermoplastic Polyurethane (TPU), and/or Engineered Thermoplastic Polyurethane (ETPU), or any suitable combination thereof. In at least some exemplary embodiments, a collar holder of monitoring device 305 may be formed from silicone material. In at least some exemplary embodiments, monitoring device 305 may include plastic material that includes a Barium material (e.g., BaSO$_4$) and/or any other suitable material that may make monitoring device 305 contrast (e.g., appear with one or more colors that contrast with other objects such as an animal's body) in an X-Ray image. For example, monitoring device 305 may include any suitable material that may cause monitoring device 305 to be easily discernible (e.g., contrast with) in an X-ray or other diagnostic image of a digestive system of an animal that has eaten monitoring device 305.

User device 310 may be any suitable user device for receiving input and/or providing output (e.g., raw data or other desired information) to a user (e.g., a user 312). User device 310 may be, for example, a touchscreen device (e.g., of a smartphone, a tablet, a smartboard, and/or any suitable computer device), a computer keyboard and monitor (e.g., desktop or laptop), an audio-based device for entering input and/or receiving output via sound, a tactile-based device for entering input and receiving output based on touch or feel, a dedicated user device or interface designed to work specifically with other components of system 300, and/or any other suitable user device or interface. For example, user device 310 may include a touchscreen device of a smartphone or handheld tablet. For example, user device 310 may include a display that may include a graphical user interface to facilitate entry of input by a user and/or receiving output. For example, system 300 may provide notifications to a user via output transmitted to user device 310.

In at least some exemplary embodiments, user device 310 may include specialized software and be registered with system 300 based on an operation of the exemplary disclosed module described below. User device 310 may allow pairing with one or more monitoring devices 305 via the exemplary disclosed module (e.g., a Bluetooth module as described below).

System 300 may include one or more modules that may be partially or substantially entirely integrated with one or more components of system 300 such as, for example, user devices 310 and/or 320, one or more monitoring devices 305, and/or any of the exemplary networks (e.g., cloud-based) described herein. The one or more modules may be software modules as described for example below regarding FIG. 5. For example, the one or more modules may include computer-executable code stored in non-volatile memory. The one or more modules may also include a processor, or alternatively, a processor for processing data associated with system 300 that may be partially or substantially entirely integrated into any portion (e.g., or combination of portions) of system 300. The one or more modules (e.g., a module for Bluetooth communication, a module for Wi-Fi communication, a module for executing the exemplary disclosed algorithms, and/or any other suitable module) may store data and/or be used to control some or all of the exemplary disclosed processes described herein.

User device 320 may be similar to user device 310. User device 320 (e.g., and/or user device 310) may also be any suitable accessory such as a smart watch, Bluetooth headphones, and/or other suitable devices that may be detected by monitoring device 305 (e.g., via Bluetooth operation). For example, user device 320 may act as a Bluetooth beacon (e.g., facilitating operation of system 300 between monitoring device 305, user device 310, communication system 315, and/or user device 320). For example, user device 320 may act as Bluetooth beacon device to indirectly connect monitoring device 305 and user device 310. In at least some exemplary embodiments, user device 320 may be detected by monitoring device 305 via communication system 315 (e.g., via Bluetooth coverage), so that user device 320 may thereby act as a Bluetooth beacon in determining a safe status of animal 308 as described herein.

Communication system 315 may provide any suitable communication such as, for example, Bluetooth communication coverage, Near Field Communication, and/or any other desired communication. Communication system 315 may be any suitable wireless system that allows exchange of data between monitoring devices 305, user devices 310, and/or user devices 320 using radio waves (e.g., short-wavelength radio waves such as UHF waves) over short distances (e.g., up to about 10 meters, and/or up to about 100 meters).

Communication system 325 may be any suitable network communication system such as a Wi-Fi network. For example, communication system 325 may be any suitable radio communication system for providing wireless local area networking of monitoring devices 305, user devices 310, and/or user devices 320.

Figure 3:
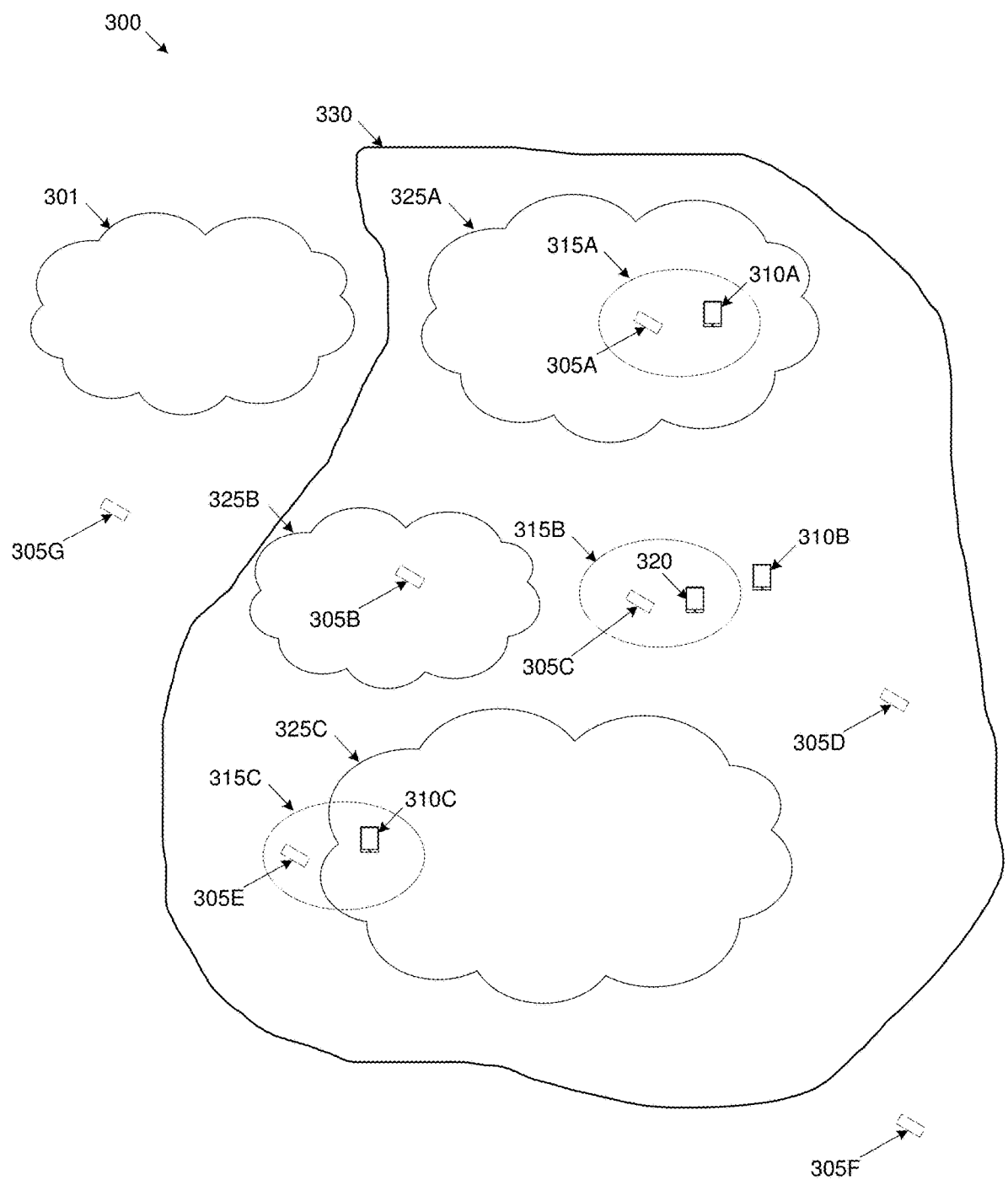
FIG. 3 illustrates an exemplary disclosed system of at least some exemplary embodiments of the present disclosure.

FIG. 3 illustrates another exemplary configuration of system 300 that may include a plurality of monitoring devices 305A, 305B, 305C, 305D, 305E, 305F, and 305G that may be similar to monitoring device 305 (e.g., and that may each be attached to, embedded in, or worn by animals 308), a plurality of user devices 310A, 310B, and 310C that may be similar to user device 310 (e.g., and that each may be associated with a user), a plurality of communication systems 315A, 315B, and 315C that may be similar to communication system 315, and a plurality of communication systems 325A, 325B, and 325C that may be similar to communication system 325. Some or all exemplary disclosed components of system 300 may also be in communication with a network 301 (e.g., the Internet or other suitable communication network as disclosed for example herein). Information may be exchanged over network 301 through one or more high speed connections such as over-the-air (OTA) connections. The exemplary disclosed monitoring devices and user devices illustrated in FIG. 3 may represent separate devices and/or various locations of the same device or devices.

FIG. 3 also illustrates a zone 330. Zone 330 may be for example a safe zone that may be safe for animals 308. Zone 330 may be defined by data (e.g., spatial data such as cartesian coordinates) that may be stored and/or processed by the exemplary disclosed modules of system 300. Zone 330 may be static and/or change dynamically over time based on an operation of system 300. Zone 330 may be based on user input, predetermined criteria, and/or artificial intelligence operations of system 300 as described for example below. Zone 330 may define (e.g., geographically define) a geographic area such as a land area, water area, and/or any other suitable geographic location. Zone 330 may be any desired size such as less than 100 square feet (SF), up to about 1,000 SF, up to about 10,000 SF (e.g., about 8,000 SF), or larger (e.g., one or more acres or one or more square miles). Zone 330 may define a safe zone for animals 308 such as a user's yard, a safe grazing area for animals, a safe terrain area, and/or safe area for animals 308 to walk, run, swim, and/or fly. Zone 330 may for example define safe areas for animals 308 based on environmental, legal, ecological, and/or any other desired criteria. In at least some exemplary embodiments, zone 330 may be a "safe" zone for animal 308 such as an apartment, a house, a suburban area, an aviary, a pen, a yard, or any other desired location.

The exemplary disclosed system, apparatus, and method may be used in any suitable application for monitoring an animal status. For example, the exemplary disclosed system, apparatus, and method may be used in any suitable application for monitoring and/or determining whether a status of an animal is safe or unsafe for example depending on geographic location, surrounding conditions, and/or any other suitable factors. The exemplary disclosed system, apparatus, and method may be used in any suitable application involving animal status monitoring such as, for example, maintaining a pet in a yard or other predetermined area, maintaining livestock, managing tracked animals (e.g., such as endangered species), and/or any other desired application for monitoring animal statuses.

Figure 4:
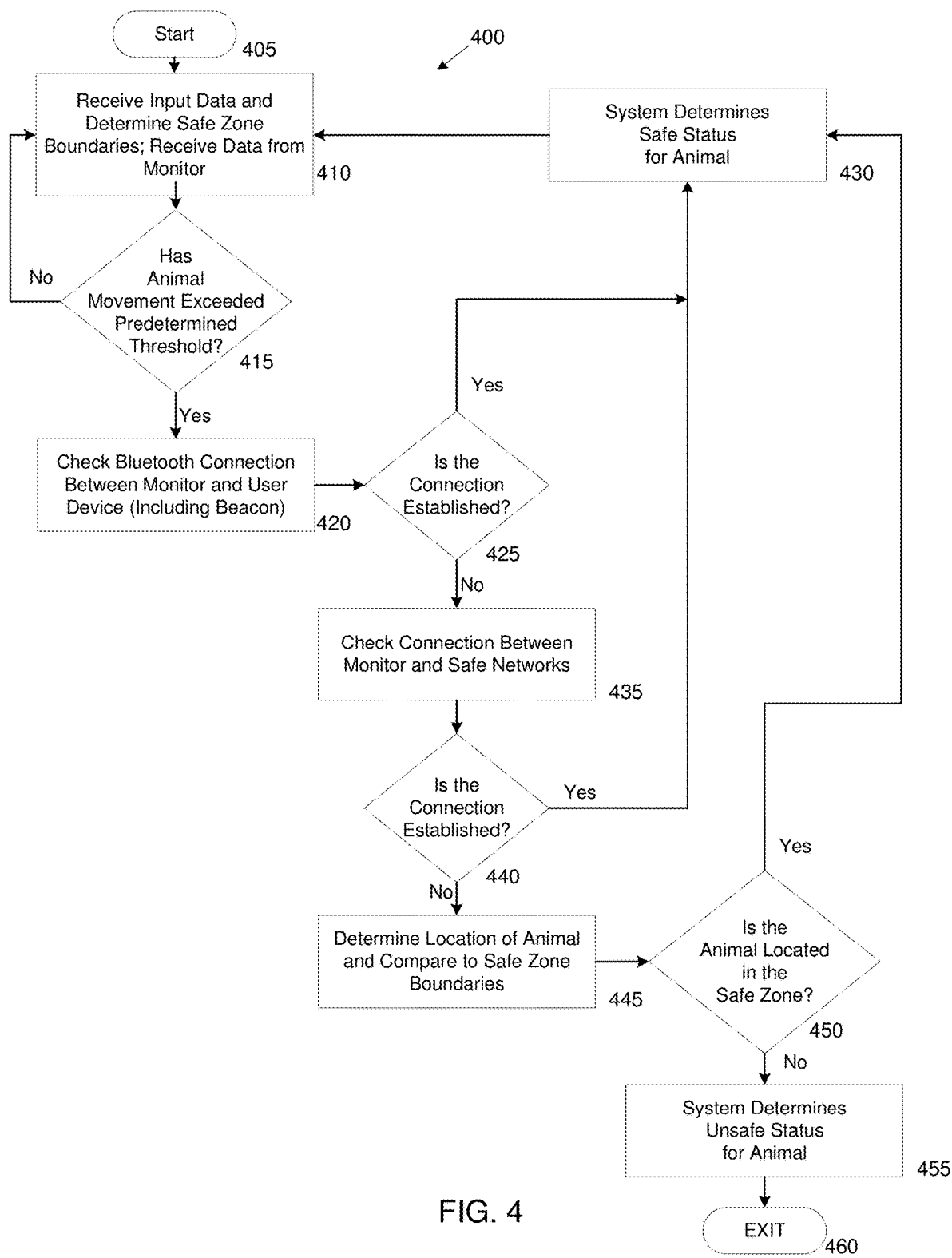
FIG. 4 illustrates an exemplary process of at least some exemplary embodiments of the present disclosure.

FIG. 4 illustrates an exemplary operation or algorithm of the exemplary disclosed system 300. Process 400 begins at step 405.

At step 410, system 300 may receive input data (e.g., from a user or other suitable source) and determine boundaries (e.g., geographic data such as 2-dimensional and/or 3-dimensional spatial coordinate data) of zone 330. System 300 may also receive data from the exemplary disclosed monitoring devices (e.g., monitoring devices 305, 305A, 305B, 305C, 305D, 305E, 305F, and/or 305G) and/or exemplary disclosed user devices (e.g., user devices 310, 310A, 310B, 310C, and/or 320).

For example at step 410, one or more users (e.g., user 312) such as owners of one or more animals 308 may register their respective user device 310 (e.g., and/or user device 320) with system 300. For example, user 312 may communicate with one or more modules of system 300 via any of the exemplary disclosed communication systems (e.g., as disclosed herein) to provide data identifying the user, user devices 310 and/or 320, the exemplary disclosed monitoring devices, animals 308, communication systems (e.g., as disclosed herein), and/or zone 330. User 312 may obtain an account via one or more modules of system 300. User 312 may pair respective user devices 310 and/or 320 with respective exemplary disclosed monitoring devices. For example, a connection may be established between respective exemplary disclosed monitoring devices and user devices.

Each user 312 may input data defining zone 330 (e.g., which may be a "safe" area that does not pose risk of injury or death to animals 308). User 312 may draw zone 330 using the exemplary disclosed user device (e.g., by drawing on a map displayed by the exemplary disclosed user device based on an operation of one or more modules of system 300). For example, user 312 may map out (e.g., trace with a finger or cursor) an area on an electronic map displayed by the exemplary disclosed user device. User 312 may also enter geographic coordinates via the exemplary disclosed user device and/or utilize global positioning components of the exemplary disclosed user device as described above to transmit real-time data to system 300 defining zone 330 (e.g., walk, drive, sail, and/or fly around the perimeter of zone 330 to transfer or "draw" zone 330 in real-time or near-real-time). System 300 may also determine zone 330 based on predetermined criteria, artificial intelligence operations, user input, emergency data (e.g., flooding and/or weather data), crowd-sourced data (e.g., data provided by social networks), law enforcement or government data, and/or any other suitable source of data defining a "safe" geographic area. Zone 330 may be defined by any suitable technique for defining a geographic area or space. Zone 330 may be updated at any time during an operation of system 300 using the exemplary techniques described above.

In at least some exemplary embodiments, zone 330 may be made by a user selecting a specific area on a map via the exemplary disclosed user device (e.g., an electronic device or other device as disclosed for example herein). For example, the choice of a specific area on the map by a user may be made by selecting a specific area on a map through an electronic device and/or by listing coordinates (e.g., GNSS and/or GPS coordinates) of certain areas that define a safe zone for one or more animals 308.

Networks may also be identified at step 410. For example a user may input and/or system 300 may detect exemplary disclosed "safe" communication systems (e.g., communication systems 315, 315A, 315B, 315C, 325, 325A, 325B, and/or 325C) operating in or near zone 330. The exemplary "safe" communication systems may be identified based on user input, being registered with system 300, meeting predetermined criteria such as entities operating the systems, and/or any other suitable technique. For example, one or more modules of system 300 (e.g., as described above) such as a Wi-Fi (e.g., and/or Bluetooth) module of system 300 may operate to detect and store data of (e.g., list) exemplary disclosed "safe" communication systems. If an unknown Wi-Fi network is detected in zone 330, the Wi-Fi network may be added to a list of "safe" Wi-Fi networks via an operation of system 300.

In at least some exemplary embodiments, the determination of safe communication systems (e.g., Wi-Fi networks) may include detecting Wi-Fi networks operating in zone 330 and including these networks in a list of "safe" networks that may be stored by one or more modules of system 300. For example, a list of safe networks may be stored (e.g., kept) in an internal storage of the exemplary disclosed monitoring device and/or any other suitable component of system 300. For example, a list of safe network access points (e.g., safe Wi-Fi access points having credentials and cartesian coordinates) may be stored on a back end of system 300, and the back end of system 300 may deliver these safe zones to one or more monitoring devices 305. If system 300 detects new Wi-Fi networks in or near zone 330, these networks may be added to the existing (e.g., already-created) list of "safe" Wi-Fi networks, which may further reduce a risk of error in the determination of the safe or unsafe status of animal 308.

One or more exemplary disclosed monitoring devices (e.g., monitoring devices 305, 305A, 305B, 305C, 305D, 305E, 305F, and/or 305G) and/or one or more exemplary disclosed user devices (e.g., user devices 310, 310A, 310B, 310C, and/or 320) may transmit and/or receive data from each other via the exemplary disclosed communication systems (e.g., communication systems 315, 315A, 315B, 315C, 325, 325A, 325B, and/or 325C) and/or network 301 at step 410 as well as any other step of process 400. Connections may be made between the exemplary disclosed devices in any suitable order. For example, an exemplary disclosed user device may connect to an exemplary disclosed monitoring device, and then the exemplary disclosed monitoring device may connect to any exemplary disclosed communication network for example as described herein (e.g., Wi-Fi, BLE, and/or any other suitable network). Also for example, an exemplary disclosed monitoring device may connect to an exemplary disclosed user device, and then the exemplary disclosed monitoring device may connect to any exemplary disclosed communication network for example as described herein (e.g., Wi-Fi, BLE, and/or any other suitable network). Animals 308 may be initially identified by system 300 to be in a safe status by system 300 (e.g., a back end of system 300 such as a back end of network 301) and/or may have their initial statuses verified by system 300 based on an operation of system 300 as described for example herein. For example, a back end of system 300 (e.g., a back end of an exemplary disclosed network for example as described herein) may make decisions of process 400 based on data received from the exemplary disclosed monitoring devices and user devices.

At step 415, system 300 may determine whether a movement of one or more animals 308 has exceeded a predetermined threshold. The exemplary disclosed monitoring devices (e.g., monitoring devices 305, 305A, 305B, 305C, 305D, 305E, 305F, and/or 305G) may detect animal movement using the exemplary disclosed sensors described above (e.g., via an accelerometer, location sensor, inclinometer, heartbeat sensor, and/or any other suitable technique as described for example herein). If animal 308 moves more than (or has a sensed attribute exceeding) a threshold such as a predetermined threshold, then process 400 may proceed to step 420. If animal 308 does not move more than a predetermined threshold, then process 400 may return to step 410.

Any suitable predetermined threshold may be set for a movement of animal 308. For example, the predetermined threshold may be set based on user input, predetermined criteria (e.g., based on animal type), and/or artificial operations of system 300 as described for example below. The threshold (e.g., predetermined threshold) may be animal 308 moving continuously for 15 seconds or moving for 15 seconds within one minute. The threshold may also be animal 308 moving more than a certain overall distance (e.g., 10 feet, 20 feet, 100 feet, or any other desired distance) during process 400 or during a certain time period (e.g., during a time period of ten minutes, 30 minutes, an hour, or any other desired time period). For example, system 300 may initially measure a movement of a given animal associated with a given monitoring device based on the number of physical steps or paces taken by the animal. For example, the number of physical steps or paces taken by the animal may be converted to linear distance (e.g., mileage or any other suitable measure of distance) based on a predetermined formula that accounts for attributes such as animal type, breed type, animal age, and/or animal height. The threshold may also be based on any other data sensed by the exemplary disclosed monitoring device (e.g., monitoring device 305, 305A, 305B, 305C, 305D, 305E, 305F, and/or 305G) such as a certain body temperature of animal 308, a certain ambient illumination (e.g., at dusk, dawn, or any other desired time), or any other desired threshold based on sensed data.

In at least some exemplary embodiments, the determination of a status of animal 308 may be made when the exemplary disclosed threshold is exceeded (e.g., when prolonged continuous movement of animal 308 is sensed). Accordingly, a status (e.g., safe or unsafe status) of animal 308 may be determined in the case of a high probability of a status change (e.g., when animal 308 is mobile). If animal 308 does not move (e.g., is asleep) or slightly changes position (e.g., changes position of its body), the probability of a status of animal 308 may be low and a status may not be checked in this situation or case. For example, conditions of prolonged continuous movement of animal 308 may be determined by the exemplary disclosed monitoring device as disclosed for example herein.

Process 400 proceeds to step 420 when system 300 receives data (e.g., from the exemplary disclosed monitoring device) that the exemplary disclosed threshold is exceeded. At step 420, system 300 may check a connection (e.g., Bluetooth connection) between the exemplary disclosed monitoring device (e.g., monitoring devices 305, 305A, 305B, 305C, 305D, 305E, 305F, and/or 305G) and the exemplary disclosed user device (e.g., user device 310, 310A, 310B, 310C, and/or 320).

For example as illustrated in FIG. 1, a connection (e.g., Bluetooth connection) may be confirmed between user device 310 of user 312 and monitoring device 305 attached to or worn by animal 308 via communication system 315 (e.g., Bluetooth communication). FIG. 1 illustrates an exemplary situation in which user 312 is situated in relatively close proximity to animal 308 and a safe status for animal 308 can be accordingly made based on the proximity of user 312 to animal 308 (e.g., animal 308 is safe because it is in close proximity of user 312 who may care for or protect animal 308).

Also for example as illustrated in FIG. 2, a connection (e.g., Bluetooth connection) may be confirmed between user device 320 and monitoring device 305 attached to or worn by animal 308. Because user device 320 may be a beacon device (e.g., as described for example herein) associated with user device 310 and user 312, system 300 may confirm a connection (e.g., Bluetooth connection) exists similar to as illustrated in FIG. 1. For example, if there is no direct connection between monitoring device 305 and user device 310 via communication system 315 (e.g., Bluetooth communication), system 300 may determine whether other devices (e.g., Beacon devices) such as user device 320 as described for example above are in communication with monitoring device 305 via communication system 315. As illustrated in FIG. 2, user device 320 may be used as a Bluetooth beacon. For example, system 300 may communicate with monitoring device 305 and user devices 310 and 320 to confirm a presence of user 312 near animal 308 (e.g., system 300 queries data from the devices to confirm the proximity of user 312 to animal 308). User devices 310 and 320 may be associated with a single user 312 or multiple users 312. For example, any desired number of users 312 (e.g., owners or trusted users) may be associated with a given animal 308. Because user devices may be registered with system 300 as described herein (e.g., and assuming users 312 have provided permission for access), system 300 may query user devices 310 and 320 and monitoring device 305 to confirm the proximity of one or more users 312 to animal 308. Accordingly, system 300 may utilize any suitable user devices such as Bluetooth beacons at step 420.

At step 425, system 300 may determine whether or not the connection checked for at step 420 has been established (e.g., been made). If the connection has not been made, process 400 may proceed to step 435. If the connection has been made, process 400 may proceed to step 430, in which system 300 may determine and record that animal 308 is in a safe status. System 300 may make such a determination for any desired number of animals 308.

In at least some exemplary embodiments at step 425, if monitoring device 305 is connected to user device 310 via Bluetooth (e.g., as illustrated in FIG. 1 or 2), process 400 may proceed to step 430 at which system 300 determines the presence of user 312 (e.g., an animal owner) nearby animal 308 and eliminates the activity of further determining the safe status of an animal, which may reduce a risk of errors in determining a status of animal 308 (e.g., avoiding false alarms and incorrect status reports). For example, system 300 may thereby reduce a risk of erroneous determinations of safe and/or unsafe statuses of one or more animals 308.

At step 435, system 300 may check a connection (e.g., wireless connection such as a Wi-Fi connection) between the exemplary disclosed monitoring device (e.g., monitoring devices 305, 305A, 305B, 305C, 305D, 305E, 305F, and/or 305G) and the exemplary disclosed communication system (e.g., communication system 325, 325A, 325B, and/or 325C). For example as illustrated in FIG. 2, in addition to being in Bluetooth communication with user device 310 via user device 320 acting as a Bluetooth beacon, monitoring device 305 may be in communication (e.g., Wi-Fi communication) with communication system 325.

Also for example as illustrated in FIG. 3, in addition to being in Bluetooth communication with user device 310A, monitoring device 305A may be in communication (e.g., Wi-Fi communication) with communication system 325A. Monitoring device 305B may be in communication (e.g., Wi-Fi communication) with communication system 325B. Monitoring devices 305C and 305E may be in Bluetooth communication (e.g., via respective communication systems 315B and 315C) but may not be in Wi-Fi communication via an exemplary disclosed communication system (e.g., communication systems 325, 325A, 325B, and 325C). Also for example, monitoring devices 305D, 305F, and 305G may be in neither Bluetooth nor Wi-Fi communication.

Process 400 may proceed to step 440, at which system 300 may determine whether or not (e.g., for exemplary disclosed monitoring devices for which there is no connection such as a Bluetooth connection as determined at steps 420 and 425) a connection identified at step 435 is established. For example as described above and as illustrated in FIG. 3, no connection such as a Bluetooth connection is established for monitoring devices 305B, 305D, 305F, and 305G. Monitoring devices 305A, 305C, and 305E may be determined as having a safe status per steps 420 and 425 above. As monitoring device 305B may be in communication such as Wi-Fi communication via communication system 325B (e.g., a "safe" Wi-Fi system), process 400 may proceed to step 430 for monitoring device 305B and a safe status may be determined for monitoring device 305B.

In at least some exemplary embodiments, if a connection between a monitoring device (e.g., monitoring device 305B) and the exemplary disclosed user device has not been established via the connection described above at steps 420 and 425 (e.g., a Bluetooth connection), then a safe status may be assigned to animal 308 in the presence of a connection to a "safe" Wi-Fi network (e.g., communication system 325A, 325B, or 325C). Also for example, a safe status may be assigned to animal 308 when a safe Wi-Fi SSID (service set identifier) is set up without cartesian coordinates (e.g., without coordinates of zone 330). For example, setting up the safe SSID may provide the safe status. For example, communication system 325B may be a "safe" Wi-Fi network that allows a determination of animal 308 via a Wi-Fi module of monitoring device 305B. Also for example, a safe status may be assigned to an animal if there is a connection to a single Wi-Fi network of the safe zone (e.g., communication system 325B) or a plurality of safe communication systems (e.g., Wi-Fi networks). Also for example, a safe status may be assigned to animal 308 when a safe Wi-Fi SSID (service set identifier) is set up. This may further reduce a risk of erroneous determination of a safe status of an animal. A user and/or system 300 may choose one or several "safe" networks, such as "safe" Wi-Fi networks, at step 410.

As described above and as illustrated in FIG. 3, monitoring devices 305D, 305F, and 305G may be in neither communication as described at steps 415 and 420 (e.g., Bluetooth communication) nor communication as described at steps 435 and 440 (e.g., Wi-Fi communication). Process 400 may proceed to step 445 for monitoring devices 305D, 305F, and 305G.

At step 445, system 300 may determine a location of one or more animals 308 via receiving location data (eg., or other sensed data as described herein) from respective exemplary disclosed monitoring devices, and compare the location data (e.g., or other sensed data) to geographic data of zone 330 (e.g., or other predetermined criteria or data as described for example herein).

For example, system 300 may query monitoring devices 305D, 305F, and 305G for location data of respective animals 308 (e.g., as sensed by sensors and components as described above). System 300 may use one or more modules such as for example described herein to determine whether each of monitoring devices 305D, 305F, and 305G worn by, embedded in, or attached to animals 308 are located in zone 330 (e.g., in the area within or bounded by zone 330 or any other zone selected by the user). The determination may be made using, for example, a cartesian coordinate system or other suitable mathematical techniques.

In at least some exemplary embodiments, if a connection between an exemplary disclosed monitoring device and communication systems described at steps 415 and 420 above (e.g., Bluetooth connection) and at steps 435 and 440 above (e.g., "safe" Wi-Fi network connection) has not been established, a "safe" status may be assigned by system 300 to a given animal 308 when coordinates of the location of the given animal 308 (e.g., based on data from a respective monitoring device of that animal 308) is in the area or range of any of the safe zones 330 added by the user. This operation may allow the presence of a given animal 308 in zone 330 (e.g., a "safe" zone) to be determined and a "safe" status assigned and recorded for the given animal 308 using one or more modules (e.g., a GNSS module and/or a GPS module) of an exemplary disclosed monitoring device and/or other component of system 300 as described for example herein. If the coordinates of a location of a given animal 308 is not in the area or range of zone 330 (e.g., the safe zone coordinates), an "unsafe" status may be assigned and recorded for the given animal 308 and an alarm notification (e.g., a phone call, text, application notification, or other suitable notification or alert) may be provided by system 300 to a given user 312 via a respective exemplary disclosed user device.

Process 400 may proceed to step 450, at which system 300 may determine whether a given animal 308 is located in zone 330 (or meets other suitable criteria) based on lcoation data (e.g., or other suitable data) provided by the exemplary disclosed monitoring device. For example as illustrated in FIG. 3, location data sensed and/or provided by monitoring device 305D attached to, embedded in, or worn by a respective animal 308 may indicate that the respective animal 308 is located in zone 330 (the "safe" zone). Process 400 may proceed to step 430 for monitoring device 305D, and system 300 may determine a "safe" status for the respective animal 308 of monitoring device 305D. Location data sensed by monitoring devices 305F and 305G may indicate respective animals 308 associated with these devices are not located within zone 330. Process 400 may proceed to step 455 for monitoring devices 305F and 305G, and system 300 may determine an "unsafe" status for the respective animals 308 of monitoring devices 305F and 305G. System 300 may also issue alert or alarm notifications to the respective users paired or associated with animals 308 of monitoring devices 305F and 305G by transferring data to exemplary disclosed user devices of those users. Process 400 may end at step 460.

In at least some exemplary embodiments, the exemplary disclosed method may include detection of a user's electronic device and determination of the safe zone of an animal location and safe Wi-Fi networks. The determination of the safe status of an animal may be carried out upon prolonged continuous movement of the animal. Accordingly, an initially safe status may be assigned to an animal when there is a connection between an electronic monitoring device and a user's electronic device through Bluetooth. If there is no connection between a monitoring device and a user's electronic device, the safe status may be assigned to an animal when an electronic monitoring device is connected to a safe Wi-Fi network. If there is no connection between an electronic monitoring device and a safe Wi-Fi network, a safe status may be assigned to an animal when GNSS coordinates of the animal's location are detected in the range of GNSS safe zone coordinates.

In at least some exemplary embodiments, the exemplary disclosed system, apparatus, and method may include determination of a safe status of an animal that is carried out based on prolonged continuous movement of the animal, which may eliminate the step of checking the status of an animal if it is stationary and/or if there is insignificant, discrete, and/or non-continuous activity of an animal (e.g., when the probability of changing the status from safe to unsafe is low or extremely low). Accordingly, errors in determining a safe status of an animal may be reduced or avoided, thereby reducing (e.g., initially reducing) the risk of an error at one or more stages of the exemplary disclosed method.

In at least some exemplary embodiments, a safe status may be initially assigned to an animal when there is a connection between a monitoring device attached to or worn by the animal and a user's electronic device via Bluetooth, which may provide the ability to detect an owner near an animal and thereby assign the safe status to an animal without further method or process steps. If a connection between a monitoring device and a user's electronic device via Bluetooth has not been established, the safe status may be assigned to an animal when there is a connection between the monitoring device and one or more safe Wi-Fi networks. This may allow (e.g., in the absence of an animal owner located nearby the animal) for assigning the safe status to the animal by detecting the animal within the coverage area (e.g., "safe" zone) of one or more safe Wi-Fi networks and then performing a safe status check for the animal. If there is no connection between an electronic monitoring device and one or more "safe" Wi-Fi networks, the safe status may be assigned to an animal when the coordinates of the animal location are detected in the range of safe zone coordinates. This may allow for the completion of the process, including assigning the safe or unsafe status to an animal and, if the animal's status is unsafe, notifying an owner of an animal of the unsafe status by sending a notification to his or her exemplary disclosed user device (e.g., electronic device).

In at least some exemplary embodiments, the exemplary disclosed method determine the safe status of an animal when the probability of a status change is relatively high or highest, which may reduce (e.g., initially reduce) the amount of times or iterations for operating the status check system, which may reduce the risk of incorrect determination of the unsafe status of an animal. The exemplary disclosed system and method may also extend (e.g., significantly extend) a battery life of an exemplary disclosed monitoring device. Determination of the safe status at each stage of the exemplary disclosed method may allow for stopping the exemplary check process and running it from the beginning at suitable times or stages. Step-by-step checking allows for determining the current status of an animal and avoiding the collection and/or processing of large amounts of data (bulk data) that may be received from an electronic monitoring device. This may reduce the risk of inaccurate determination of an animal's safe status, which may achieve the result (e.g., technical result) of reducing the risk of error when determining the status of an animal while increasing battery life (e.g., so that the quality of determining the safe status of an animal is improved).

In at least some exemplary embodiments, the exemplary disclosed method may allow for the exclusion of repeatedly determining the safe status of a sleeping or immobile animal, which may lead to a false determination of the unsafe status (e.g., false alarms). The exemplary disclosed system, apparatus, and method may also allow for less consumption of energy, and this energy savings may allow for reducing the risk of early battery discharge of a monitoring device and may also extend the battery life of a monitoring device. This may reduce the risk of animal loss based on malfunction of the system, which may improve a quality of current status determination.

In at least some exemplary embodiments, a safe status may be checked based on the presence of a collar's connection with an electronic device of an animal owner via a BLE channel. If there is a connection with an owner's electronic device via the BLE channel, the animal status may be determined as safe. If there is no connection with an owner's electronic device via the BLE channel, Wi-Fi networks available near an animal may be checked and searched in a list of safe Wi-Fi networks. If there are available Wi-Fi networks in the list of safe networks (e.g., of safe networks during scanning of Wi-Fi networks from monitoring device 305), the animal status may be determined as safe. Additionally, the exemplary disclosed system may use data collected during a lifecycle of the exemplary disclosed monitoring device regarding Wi-Fi networks (e.g., nearby safe Wi-Fi access points and/or cartesian safe zones). For example, system 300 may use third party services (e.g., Google Geolocation API) for obtaining a geolocation of Wi-Fi access points worldwide. If there are no available Wi-Fi networks in the list of safe networks, the GNSS module may be accessed, coordinates of the animal location may be determined, and then the obtained GNSS coordinates may be searched in the coordinates of the safe zone. In case that the GNSS coordinates of the animal location were determined in the range of the safe zone coordinates, the safe status may be assigned to an animal. In the case of a discrepancy of coordinates (e.g., the animal is not located within the area defined by the coordinates), the unsafe status may be assigned to the animal, and a notification may be sent to an owner's smartphone that an animal is located outside the safe zone.

In at least some exemplary embodiments, the exemplary disclosed method may include detection of a user's electronic device, determination of the range of coordinates of the safe zone, and determination of safe Wi-Fi networks and/or other Wi-Fi networks closely located to the safe Wi-Fi access point or spatial zone. The exemplary disclosed method may be carried out with prolonged continuous movement of an animal. Accordingly, an initially safe status may be assigned to an animal when there is a connection between an electronic monitoring device and a user's electronic device via Bluetooth. If there is no connection between a monitoring device and a user's electronic device, the safe status may be assigned to an animal when an electronic monitoring device is connected to the safe Wi-Fi network. If there is no connection between an electronic monitoring device and the safe Wi-Fi network, the safe status may be assigned to an animal when GNSS coordinates of the animal location are detected in the range of the GNSS safe zone coordinates. The prolonged continuous movement of an animal may be determined by the data of the duration of movement and the overload received from an accelerometer of an electronic monitoring device. Determination of the safe zone of the animal location may be carried out by a user by selecting a specific area on the map through an electronic device. If there is no Bluetooth connection between an electronic monitoring device and a user's electronic device, the presence of other electronic devices in the Bluetooth coverage area may be checked. In case the other devices are detected, these other devices may be used as Bluetooth beacons. If an unknown Wi-Fi network is detected in the safe zone, the exemplary disclosed system may obtain and use information associated with the unknown Wi-Fi network to analyze an area in which an exemplary disclosed user device is located (e.g., an area that may be difficult for receiving a GPS signal). A user may select any desired "safe" Wi-Fi networks. If one or more of the "safe" Wi-Fi networks is detected, a safe status may be assigned to an animal.

In at least some exemplary embodiments, the exemplary disclosed method may include providing a monitoring device (e.g., monitoring device 305, 305A, 305B, 305C, 305D, 305E, 305F, or 305G) to an animal, the animal being monitored by a user having a user device, determining location data defining a spatial zone (e.g., zone 330), determining location data of the monitoring device, sensing a movement of the animal using the monitoring device, and determining whether or not the monitoring device is connected to the user device via a first communication system when the movement of the animal exceeds a movement threshold. The exemplary disclosed method may also include determining whether or not the monitoring device is connected to a second communication system (e.g., as further described below) when the monitoring device is not connected to the user device via the first communication system, determining whether or not the monitoring device is located in the spatial zone by comparing the location data defining the spatial zone with the location data of the monitoring device, transferring alert data to the user device when the monitoring device is not located in the spatial zone, and controlling an accessory, which is connected to the monitoring device, based on the alert data. The accessory may be a Bluetooth flashlight and controlling the Bluetooth flashlight includes emitting light that indicates an alert or a safe status of the animal. The first communication system may be a Bluetooth system. The second communication system may be a Wi-Fi network. The exemplary disclosed method may also include transmitting data to the user device indicating a safe status for the animal when the movement of the animal is less than the movement threshold. The exemplary disclosed method may further include transmitting data to the user device indicating a safe status for the animal when the monitoring device is connected to the user device via the first communication system and maintaining the safe status until the movement of the animal exceeds the movement threshold. The exemplary disclosed method may additionally include transmitting data to the user device indicating a safe status for the animal when the monitoring device is connected to the second communication system and maintaining the safe status until the movement of the animal exceeds the movement threshold. The exemplary disclosed method may also include transmitting data to the user device indicating a safe status for the animal when the monitoring device is located in the spatial zone and maintaining the safe status until the movement of the animal exceeds the movement threshold. Sensing a movement of the animal using the monitoring device may include using an accelerometer included in the monitoring device. Determining location data of the monitoring device may include using a positioning system selected from the group consisting of GNSS and GPS. The exemplary disclosed method may also include pairing the user device that is a smartphone with the monitoring device that is a collar worn by the animal, wherein the animal is a pet of the user. The exemplary disclosed method may further include updating the location data defining the spatial zone that is a safe zone for the animal. The movement threshold may be the animal moving continuously for 15 seconds.

In at least some exemplary embodiments, determining whether or not the monitoring device is connected to the second communication system may also include determining whether a trusted SSID is active in the Wi-Fi coverage area of the monitoring device without being directly connected. A safe Wi-Fi AP may be used to transmit or receive some data based on some event. For example, a BLE COMMAND may not be used because BLE (e.g., Bluetooth Low Energy) speed may be relatively low and the system may use Wi-Fi to download new firmware relatively quickly. The exemplary disclosed system may also use a safe Wi-Fi AP to transmit accumulated track information if there is no BLE connection with an exemplary disclosed user device (e.g., during a walk or other activity). A BACKEND COMMAND may be received after established direct connection is made (e.g., over embedded modem and sim chip).

The exemplary disclosed system may include an animal status module (e.g., one or modules as described for example herein), comprising computer-executable code stored in non-volatile memory, a processor, a monitoring device (e.g., monitoring device 305, 305A, 305B, 305C, 305D, 305E, 305F, or 305G), and a user device. The animal status module, the processor, the monitoring device, and the user device may be configured to determine location data defining a safe geographic zone (e.g., zone 330), determine location data of the monitoring device, sense a movement of an animal using the monitoring device, and determine whether or not the monitoring device is connected to the user device via a first communication system when the movement of the animal exceeds a movement threshold. The animal status module, the processor, the monitoring device, and the user device may be configured to determine whether or not the monitoring device is connected to a second communication system (e.g., or the monitoring device is closely located to the second communication system or other similar systems without connection to the second communication system) when the monitoring device is not connected to the user device via the first communication system, determine whether or not the monitoring device is located in the safe geographic zone by comparing the location data defining the safe geographic zone with the location data of the monitoring device, and transfer alert data to the user device when the monitoring device is not located in the safe geographic zone. Each of the first communication system and the second communication system may be either a Bluetooth system or a Wi-Fi network. The animal status module, the processor, the monitoring device, and the user device may be configured to: transmit data to the user device indicating a safe status for the animal when the monitoring device is connected to the user device via the first communication system, and maintain the safe status until the movement of the animal exceeds the movement threshold (e.g., if the exemplary disclosed monitoring device is in sleep mode). The animal status module, the processor, the monitoring device, and the user device may be configured to: transmit data to the user device indicating a safe status for the animal when the monitoring device is connected to the second communication system, and maintain the safe status until the movement of the animal exceeds the movement threshold. For example, the safe status may be maintained until the monitoring device identifies (e.g., "sees") a trusted Wi-Fi AP with or without direct connection, or identifies (e.g., "sees") other Wi-Fi AP's relatively closely located to the trusted ones (e.g., or in case the exemplary disclosed monitoring device goes to sleep mode and stays in sleep mode until the movement of the animal exceeds the predetermined movement threshold). The animal status module, the processor, the monitoring device, and the user device may be configured to: transmit data to the user device indicating a safe status for the animal when the monitoring device is located in the safe geographic zone, and maintain the safe status until the movement of the animal exceeds the movement threshold. The Wi-Fi network may be located in the safe geographic zone.

In at least some exemplary embodiments, the exemplary disclosed method may include providing a monitoring device (e.g., monitoring device 305, 305A, 305B, 305C, 305D, 305E, 305F, or 305G) to an animal, the animal being monitored by a user having a user device, determining location data defining a spatial zone, determining location data of the monitoring device, sensing a movement of the animal using the monitoring device, and determining whether or not the monitoring device is directly connected to the user device via Bluetooth communication when the movement of the animal exceeds a movement threshold. The exemplary disclosed method may also include determining whether or not the monitoring device is connected to a Wi-Fi network when the monitoring device is not directly connected to the user device via Bluetooth communication, determining whether or not the monitoring device is located in the spatial zone by comparing the location data defining the spatial zone with the location data of the monitoring device, and transferring alert data to the user device when the monitoring device is not located in the spatial zone. The exemplary disclosed method may also include identifying an additional Wi-Fi network located in the spatial zone and indicating a safe status for the animal when the monitoring device is connected to the additional Wi-Fi network. The exemplary disclosed method may further include identifying a Bluetooth beacon device when the monitoring device is not directly connected to the user device via Bluetooth communication, and using the Bluetooth beacon device to indirectly connect the monitoring device to the user device.

In at least some exemplary embodiments, a BLE-connected and/or Wi-Fi-connected accessory or device such as a lighting device (e.g., flashlight), audio device (e.g., an audio emitter such as a siren), and/or any other suitable notification device may be paired with the exemplary disclosed monitoring device via the exemplary disclosed user device. The exemplary disclosed accessory may be, for example, an accessory 306 as illustrated in FIGS. 1 and 2. The exemplary device (e.g., BLE-connected and/or Wi-Fi-connected flashlight, siren, and/or other suitable device) may be connected (e.g., via BLE, Wi-Fi, other suitable network, by electrical wire, and/or physically connected) to the exemplary disclosed monitoring device. The exemplary device (e.g., BLE-connected and/or Wi-Fi-connected flashlight, siren, and/or other suitable device) may be attached to an attachment device (e.g., a metal ring) of the exemplary disclosed monitoring device. When an animal is in an unsafe condition as determined for example herein, the exemplary disclosed system may control the device (e.g., BLE-connected and/or Wi-Fi-connected flashlight, siren, and/or other suitable device) to turn on to help a user find the animal. Also for example, a user can remotely control the device (e.g., BLE-connected and/or Wi-Fi-connected flashlight, siren, and/or other suitable device) using the exemplary disclosed user device. For example a user and/or the exemplary disclosed system may control the device (e.g., BLE-connected and/or Wi-Fi-connected flashlight, siren, and/or other suitable device) to shine, emit sounds, and/or provide any other desired notification with any desired intensity and/or pattern (e.g., audio and/or blinking light pattern).

The exemplary disclosed system, apparatus, and method may provide an efficient and effective technique for improving the quality of determining a safe status of an animal. For example, the exemplary disclosed system, apparatus, and method may reduce the risk of errors in determination of the animal status, which may for example reduce a number of false alarms and other incorrect reports of animal status. The exemplary disclosed system, apparatus, and method may also reduce an amount of energy (e.g., reduce an energy intensity) used in determining an animal status.

Figure 5:
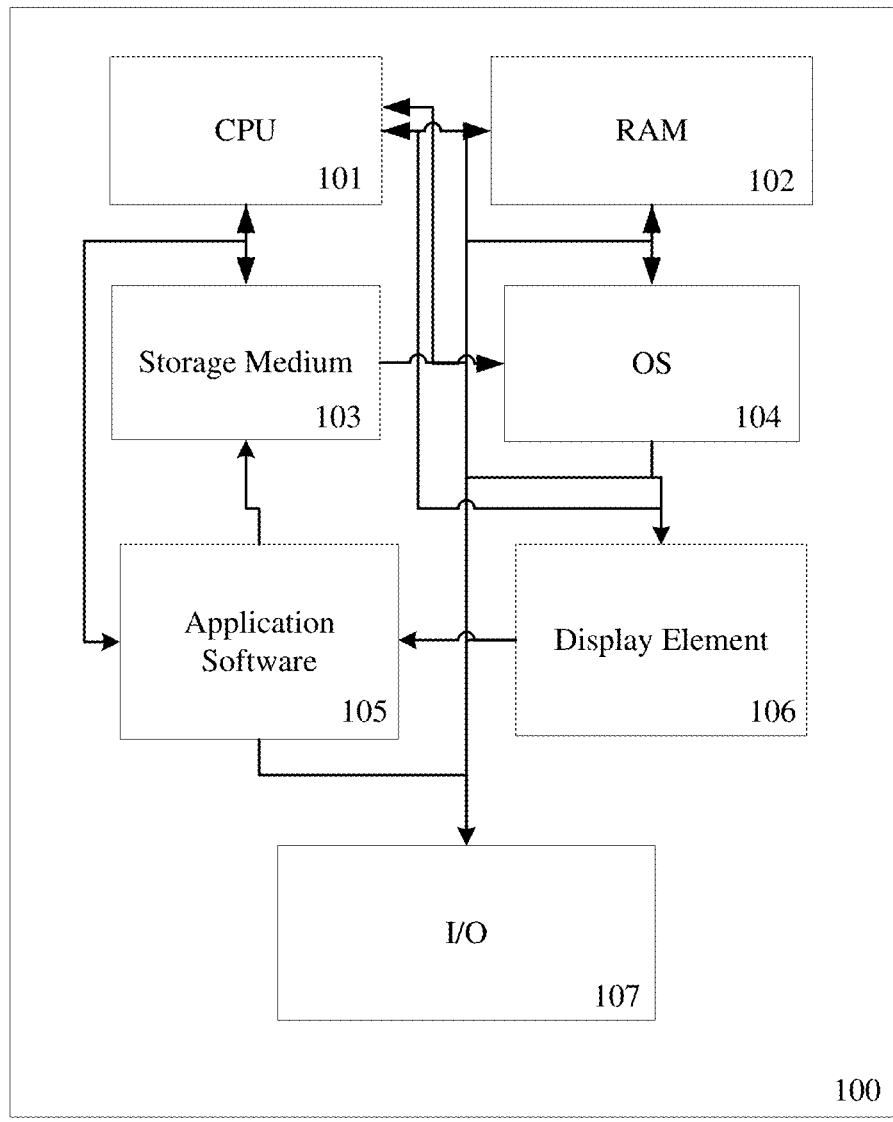
FIG. 5 is a schematic illustration of an exemplary computing device, in accordance with at least some exemplary embodiments of the present disclosure.

An illustrative representation of a computing device appropriate for use with embodiments of the system of the present disclosure is shown in FIG. 5. The computing device 100 can generally be comprised of a Central Processing Unit (CPU, 101), optional further processing units including a graphics processing unit (GPU), a Random Access Memory (RAM, 102), a mother board 103, or alternatively/additionally a storage medium (e.g., hard disk drive, solid state drive, flash memory, cloud storage), an operating system (OS, 104), one or more application software 105, a display element 106, and one or more input/output devices/means 107, including one or more communication interfaces (e.g., RS232, Ethernet, Wi-Fi, Bluetooth, USB). Useful examples include, but are not limited to, personal computers, smart phones, laptops, mobile computing devices, tablet PCs, touch boards, and servers. Multiple computing devices can be operably linked to form a computer network in a manner as to distribute and share one or more resources, such as clustered computing devices and server banks/farms.

Various examples of such general-purpose multi-unit computer networks suitable for embodiments of the disclosure, their typical configuration and many standardized communication links are well known to one skilled in the art, as explained in more detail and illustrated by FIG. 6, which is discussed herein-below.

According to an exemplary embodiment of the present disclosure, data may be transferred to the system, stored by the system and/or transferred by the system to users of the system across local area networks (LANs) (e.g., office networks, home networks) or wide area networks (WANs) (e.g., the Internet). In accordance with the previous embodiment, the system may be comprised of numerous servers communicatively connected across one or more LANs and/or WANs. One of ordinary skill in the art would appreciate that there are numerous manners in which the system could be configured and embodiments of the present disclosure are contemplated for use with any configuration.

In general, the system and methods provided herein may be employed by a user of a computing device whether connected to a network or not. Similarly, some steps of the methods provided herein may be performed by components and modules of the system whether connected or not. While such components/modules are offline, and the data they generated will then be transmitted to the relevant other parts of the system once the offline component/module comes again online with the rest of the network (or a relevant part thereof). According to an embodiment of the present disclosure, some of the applications of the present disclosure may not be accessible when not connected to a network, however a user or a module/component of the system itself may be able to compose data offline from the remainder of the system that will be consumed by the system or its other components when the user/offline system component or module is later connected to the system network.

Figure 6:
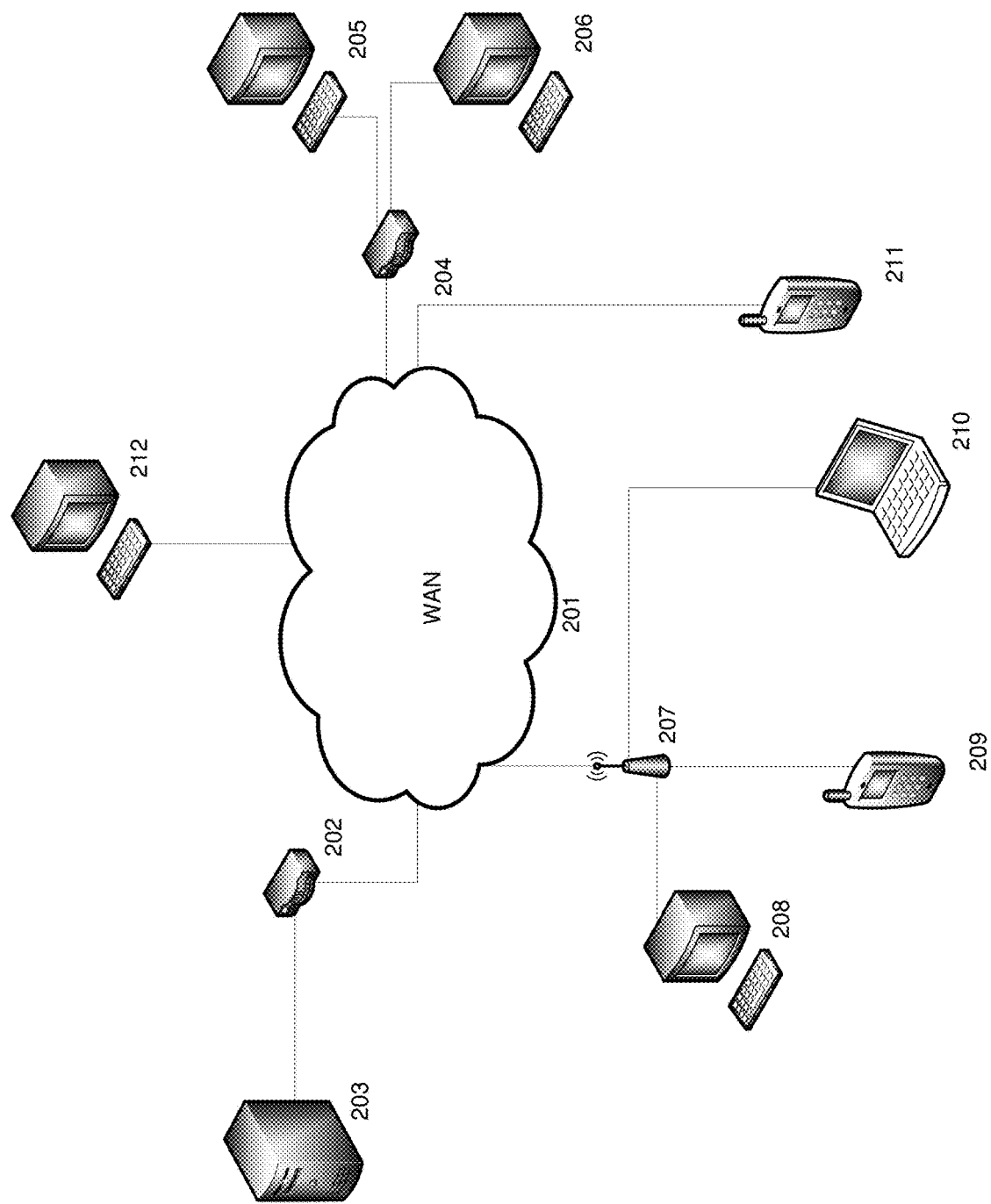
FIG. 6 is a schematic illustration of an exemplary network, in accordance with at least some exemplary embodiments of the present disclosure.

Referring to FIG. 6, a schematic overview of a system in accordance with an embodiment of the present disclosure is shown. The system is comprised of one or more application servers 203 for electronically storing information used by the system. Applications in the server 203 may retrieve and manipulate information in storage devices and exchange information through a WAN 201 (e.g., the Internet). Applications in server 203 may also be used to manipulate information stored remotely and process and analyze data stored remotely across a WAN 201 (e.g., the Internet).

According to an exemplary embodiment, as shown in FIG. 6, exchange of information through the WAN 201 or other network may occur through one or more high speed connections. In some cases, high speed connections may be over-the-air (OTA), passed through networked systems, directly connected to one or more WANs 201 or directed through one or more routers 202. Router(s) 202 are completely optional and other embodiments in accordance with the present disclosure may or may not utilize one or more routers 202. One of ordinary skill in the art would appreciate that there are numerous ways server 203 may connect to WAN 201 for the exchange of information, and embodiments of the present disclosure are contemplated for use with any method for connecting to networks for the purpose of exchanging information. Further, while this application refers to high speed connections, embodiments of the present disclosure may be utilized with connections of any speed.

Components or modules of the system may connect to server 203 via WAN 201 or other network in numerous ways. For instance, a component or module may connect to the system i) through a computing device 212 directly connected to the WAN 201, ii) through a computing device 205, 206 connected to the WAN 201 through a routing device 204, iii) through a computing device 208, 209, 210 connected to a wireless access point 207 or iv) through a computing device 211 via a wireless connection (e.g., CDMA, GSM, 3G, 4G) to the WAN 201. One of ordinary skill in the art will appreciate that there are numerous ways that a component or module may connect to server 203 via WAN 201 or other network, and embodiments of the present disclosure are contemplated for use with any method for connecting to server 203 via WAN 201 or other network. Furthermore, server 203 could be comprised of a personal computing device, such as a smartphone, acting as a host for other computing devices to connect to.

The communications means of the system may be any means for communicating data, including text, binary data, image and video, over one or more networks or to one or more peripheral devices attached to the system, or to a system module or component. Appropriate communications means may include, but are not limited to, wireless connections, wired connections, cellular connections, data port connections, Bluetooth® connections, near field communications (NFC) connections, or any combination thereof. One of ordinary skill in the art will appreciate that there are numerous communications means that may be utilized with embodiments of the present disclosure, and embodiments of the present disclosure are contemplated for use with any communications means.

The exemplary disclosed system may for example utilize collected data to prepare and submit datasets and variables to cloud computing clusters and/or other analytical tools (e.g., predictive analytical tools) which may analyze such data using artificial intelligence neural networks. The exemplary disclosed system may for example include cloud computing clusters performing predictive analysis. For example, the exemplary disclosed system may utilize neural network-based artificial intelligence to predictively assess risk. For example, the exemplary neural network may include a plurality of input nodes that may be interconnected and/or networked with a plurality of additional and/or other processing nodes to determine a predicted result (e.g., a location as described for example herein).

For example, exemplary artificial intelligence processes may include filtering and processing datasets, processing to simplify datasets by statistically eliminating irrelevant, invariant or superfluous variables or creating new variables which are an amalgamation of a set of underlying variables, and/or processing for splitting datasets into train, test and validate datasets using at least a stratified sampling technique. For example, the prediction algorithms and approach may include regression models, tree-based approaches, logistic regression, Bayesian methods, deep-learning and neural networks both as a stand-alone and on an ensemble basis, and final prediction may be based on the model/structure which delivers the highest degree of accuracy and stability as judged by implementation against the test and validate datasets. Also for example, exemplary artificial intelligence processes may include processing for training a machine learning model to make predictions based on data collected by the exemplary disclosed sensors.

Traditionally, a computer program includes a finite sequence of computational instructions or program instructions. It will be appreciated that a programmable apparatus or computing device can receive such a computer program and, by processing the computational instructions thereof, produce a technical effect.

A programmable apparatus or computing device includes one or more microprocessors, microcontrollers, embedded microcontrollers, programmable digital signal processors, programmable devices, programmable gate arrays, programmable array logic, memory devices, application specific integrated circuits, or the like, which can be suitably employed or configured to process computer program instructions, execute computer logic, store computer data, and so on. Throughout this disclosure and elsewhere a computing device can include any and all suitable combinations of at least one general purpose computer, special-purpose computer, programmable data processing apparatus, processor, processor architecture, and so on. It will be understood that a computing device can include a computer-readable storage medium and that this medium may be internal or external, removable and replaceable, or fixed. It will also be understood that a computing device can include a Basic Input/Output System (BIOS), firmware, an operating system, a database, or the like that can include, interface with, or support the software and hardware described herein.

Embodiments of the system as described herein are not limited to applications involving conventional computer programs or programmable apparatuses that run them. It is contemplated, for example, that embodiments of the disclosure as claimed herein could include an optical computer, quantum computer, analog computer, or the like.

Regardless of the type of computer program or computing device involved, a computer program can be loaded onto a computing device to produce a particular machine that can perform any and all of the depicted functions. This particular machine (or networked configuration thereof) provides a technique for carrying out any and all of the depicted functions.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. Illustrative examples of the computer readable storage medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A data store may be comprised of one or more of a database, file storage system, relational data storage system or any other data system or structure configured to store data. The data store may be a relational database, working in conjunction with a relational database management system (RDBMS) for receiving, processing and storing data. A data store may comprise one or more databases for storing information related to the processing of moving information and estimate information as well one or more databases configured for storage and retrieval of moving information and estimate information.

Computer program instructions can be stored in a computer-readable memory capable of directing a computer or other programmable data processing apparatus to function in a particular manner. The instructions stored in the computer-readable memory constitute an article of manufacture including computer-readable instructions for implementing any and all of the depicted functions.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

The elements depicted in flowchart illustrations and block diagrams throughout the figures imply logical boundaries between the elements. However, according to software or hardware engineering practices, the depicted elements and the functions thereof may be implemented as parts of a monolithic software structure, as standalone software components or modules, or as components or modules that employ external routines, code, services, and so forth, or any combination of these. All such implementations are within the scope of the present disclosure. In view of the foregoing, it will be appreciated that elements of the block diagrams and flowchart illustrations support combinations of means for performing the specified functions, combinations of steps for performing the specified functions, program instruction technique for performing the specified functions, and so on.

It will be appreciated that computer program instructions may include computer executable code. A variety of languages for expressing computer program instructions are possible, including without limitation Kotlin, Swift, C #, PHP, C, C++, Assembler, Java, HTML, JavaScript, CSS, and so on. Such languages may include assembly languages, hardware description languages, database programming languages, functional programming languages, imperative programming languages, and so on. In some embodiments, computer program instructions can be stored, compiled, or interpreted to run on a computing device, a programmable data processing apparatus, a heterogeneous combination of processors or processor architectures, and so on. Without limitation, embodiments of the system as described herein can take the form of mobile applications, firmware for monitoring devices, web-based computer software, and so on, which includes client/server software, software-as-a-service, peer-to-peer software, or the like.

In some embodiments, a computing device enables execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more thread. The thread can spawn other threads, which can themselves have assigned priorities associated with them. In some embodiments, a computing device can process these threads based on priority or any other order based on instructions provided in the program code.

Unless explicitly stated or otherwise clear from the context, the verbs "process" and "execute" are used interchangeably to indicate execute, process, interpret, compile, assemble, link, load, any and all combinations of the foregoing, or the like. Therefore, embodiments that process computer program instructions, computer-executable code, or the like can suitably act upon the instructions or code in any and all of the ways just described.

The functions and operations presented herein are not inherently related to any particular computing device or other apparatus. Various general-purpose systems may also be used with programs in accordance with the teachings herein, or it may prove convenient to construct more specialized apparatus to perform the required method steps. The required structure for a variety of these systems will be apparent to those of ordinary skill in the art, along with equivalent variations. In addition, embodiments of the disclosure are not described with reference to any particular programming language. It is appreciated that a variety of programming languages may be used to implement the present teachings as described herein, and any references to specific languages are provided for disclosure of enablement and best mode of embodiments of the disclosure. Embodiments of the disclosure are well suited to a wide variety of computer network systems over numerous topologies. Within this field, the configuration and management of large networks include storage devices and computing devices that are communicatively coupled to dissimilar computing and storage devices over a network, such as the Internet, also referred to as "web" or "world wide web".

Throughout this disclosure and elsewhere, block diagrams and flowchart illustrations depict methods, apparatuses (e.g., systems), and computer program products. Each element of the block diagrams and flowchart illustrations, as well as each respective combination of elements in the block diagrams and flowchart illustrations, illustrates a function of the methods, apparatuses, and computer program products. Any and all such functions ("depicted functions") can be implemented by computer program instructions; by special-purpose, hardware-based computer systems; by combinations of special purpose hardware and computer instructions; by combinations of general purpose hardware and computer instructions; and so on—any and all of which may be generally referred to herein as a "component", "module," or "system."

While the foregoing drawings and description set forth functional aspects of the disclosed systems, no particular arrangement of software for implementing these functional aspects should be inferred from these descriptions unless explicitly stated or otherwise clear from the context.

Each element in flowchart illustrations may depict a step, or group of steps, of a computer-implemented method. Further, each step may contain one or more sub-steps. For the purpose of illustration, these steps (as well as any and all other steps identified and described above) are presented in order. It will be understood that an embodiment can contain an alternate order of the steps adapted to a particular application of a technique disclosed herein. All such variations and modifications are intended to fall within the scope of this disclosure. The depiction and description of steps in any particular order is not intended to exclude embodiments having the steps in a different order, unless required by a particular application, explicitly stated, or otherwise clear from the context.

The functions, systems and methods herein described could be utilized and presented in a multitude of languages. Individual systems may be presented in one or more languages and the language may be changed with ease at any point in the process or methods described above. One of ordinary skill in the art would appreciate that there are numerous languages the system could be provided in, and embodiments of the present disclosure are contemplated for use with any language.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

It will be apparent to those skilled in the art that various modifications and variations can be made to the disclosed system and method. Other embodiments will be apparent to those skilled in the art from consideration of the specification and practice of the disclosed method and apparatus. It is intended that the specification and examples be considered as exemplary only, with a true scope being indicated by the following claims.

What is claimed is:

1. A method, comprising:
providing a monitoring device to an animal, the animal being monitored by a user having a user device;
determining location data defining a spatial zone;
determining location data of the monitoring device;
sensing a movement of the animal using the monitoring device;
determining whether or not the monitoring device is connected to the user device via a first communication system when the movement of the animal exceeds a movement threshold;
determining whether or not the monitoring device is connected to a second communication system when the monitoring device is not connected to the user device via the first communication system;
determining whether or not the monitoring device is located in the spatial zone by comparing the location data defining the spatial zone with the location data of the monitoring device when the monitoring device is not connected to the second communication system;

transferring alert data to the user device when the monitoring device is not located in the spatial zone; and
controlling an accessory, which is connected to the monitoring device, based on the alert data.

2. The method of claim 1, wherein the accessory is a Bluetooth flashlight and controlling the Bluetooth flashlight includes emitting light that indicates an alert or a safe status of the animal.

3. The method of claim 1, wherein the first communication system is a Bluetooth system and the second communication system is a Wi-Fi network.

4. The method of claim 1, further comprising transmitting data to the user device indicating a safe status for the animal when the movement of the animal is less than the movement threshold, and controlling the accessory to emit light or sound indicating the safe status.

5. The method of claim 1, further comprising transmitting data to the user device indicating a safe status for the animal when the monitoring device is connected to the user device via the first communication system and maintaining the safe status until the movement of the animal exceeds the movement threshold, and controlling the accessory to emit light or sound indicating the safe status.

6. The method of claim 1, further comprising transmitting data to the user device indicating a safe status for the animal when the monitoring device is connected to the second communication system and maintaining the safe status until the movement of the animal exceeds the movement threshold, and controlling the accessory to emit light or sound indicating the safe status.

7. The method of claim 1, further comprising transmitting data to the user device indicating a safe status for the animal when the monitoring device is located in the spatial zone and maintaining the safe status until the movement of the animal exceeds the movement threshold, and controlling the accessory to emit light or sound indicating the safe status.

8. The method if claim 1, wherein sensing a movement of the animal using the monitoring device includes using an accelerometer included in the monitoring device.

9. The method of claim 1, wherein determining location data of the monitoring device includes using a positioning system selected from the group consisting of Global Navigation Satellite System (GNSS) and Global Positioning System (GPS).

10. The method of claim 1, further comprising pairing the user device that is a smartphone with the monitoring device that is a collar worn by the animal, wherein the animal is a pet of the user.

11. The method of claim 1, further comprising updating the location data defining the spatial zone that is a safe zone for the animal.

12. The method of claim 1, wherein the movement threshold is the animal moving continuously for 15 seconds.

13. A system, comprising:
an animal status module, comprising computer-executable code stored in non-volatile memory;
a processor;
a monitoring device;
an accessory that is connected to the monitoring device; and
a user device;
wherein the animal status module, the processor, the monitoring device, and the user device are configured to:
determine location data defining a safe geographic zone;
determine location data of the monitoring device;
sense a movement of an animal using the monitoring device;
determine whether or not the monitoring device is connected to the user device via a first communication system when the movement of the animal exceeds a movement threshold;
determine whether or not the monitoring device is connected to a second communication system when the monitoring device is not connected to the user device via the first communication system;
determine whether or not the monitoring device is located in the safe geographic zone by comparing the location data defining the safe geographic zone with the location data of the monitoring device when the monitoring device is not connected to the second communication system; and
transfer alert data to the user device when the monitoring device is not located in the safe geographic zone; and
control the accessory based on the alert data;
wherein each of the first communication system and the second communication system is either a Bluetooth system or a Wi-Fi network.

14. The system of claim 13, wherein the animal status module, the processor, the monitoring device, and the user device are configured to: transmit data to the user device indicating a safe status for the animal when the monitoring device is connected to the user device via the first communication system, maintain the safe status until the movement of the animal exceeds the movement threshold, and control the accessory to emit light or sound indicating the safe status.

15. The system of claim 13, wherein the animal status module, the processor, the monitoring device, and the user device are configured to: transmit data to the user device indicating a safe status for the animal when the monitoring device is connected to the second communication system, maintain the safe status until the movement of the animal exceeds the movement threshold, and control the accessory to emit light or sound indicating the safe status.

16. The system of claim 13, wherein the animal status module, the processor, the monitoring device, and the user device are configured to: transmit data to the user device indicating a safe status for the animal when the monitoring device is located in the safe geographic zone, maintain the safe status until the movement of the animal exceeds the movement threshold, and control the accessory to emit light or sound indicating the safe status.

17. The system of claim 13, wherein the second communication system is located in the safe geographic zone.

18. A method, comprising:
providing a monitoring device to an animal, the animal being monitored by a user having a user device;
determining location data defining a spatial zone;
determining location data of the monitoring device;
sensing a movement of the animal using the monitoring device;
determining whether or not the monitoring device is directly connected to the user device via Bluetooth communication when the movement of the animal exceeds a movement threshold;
determining whether or not the monitoring device is connected to a Wi-Fi network when the monitoring device is not directly connected to the user device via Bluetooth communication;
determining whether or not the monitoring device is located in the spatial zone by comparing the location data defining the spatial zone with the location data of the monitoring device when the monitoring device is not connected to the Wi-Fi network;

transferring alert data to the user device when the monitoring device is not located in the spatial zone; and controlling a Bluetooth flashlight, which is connected to the monitoring device, based on the alert data.

19. The method of claim 18, further comprising identifying an additional Wi-Fi network located in the spatial zone and indicating a safe status for the animal via the Bluetooth flashlight when the monitoring device is connected to the additional Wi-Fi network.

20. The method of claim 18, further comprising identifying a Bluetooth beacon device when the monitoring device is not directly connected to the user device via Bluetooth communication, and using the Bluetooth beacon device to indirectly connect the monitoring device to the user device.

* * * * *